(12) United States Patent
Geoffroy et al.

(10) Patent No.: US 11,386,185 B2
(45) Date of Patent: Jul. 12, 2022

(54) WEB INTELLIGENT DOCUMENT WAS A DATA SOURCE

(71) Applicant: BUSINESS OBJECTS SOFTWARE LTD., Dublin (IE)

(72) Inventors: Raphael Geoffroy, Colombes (FR); Sebastien Ducaule, Levallois Perret (FR)

(73) Assignee: BUSINESS OBJECTS SOFTWARE LTD., Dublin (IE)

( * ) Notice: Subject to any disclaimer, the term of this patent is extended or adjusted under 35 U.S.C. 154(b) by 38 days.

(21) Appl. No.: 17/070,114

(22) Filed: Oct. 14, 2020

(65) Prior Publication Data

US 2022/0113949 A1    Apr. 14, 2022

(51) Int. Cl.
| | |
|---|---|
| *G06F 9/44* | (2018.01) |
| *G06F 16/958* | (2019.01) |
| *G06F 8/36* | (2018.01) |
| *G06F 9/54* | (2006.01) |
| *G06Q 30/02* | (2012.01) |
| *G06Q 10/06* | (2012.01) |
| *A61B 5/16* | (2006.01) |
| *G06F 16/24* | (2019.01) |
| *G06F 16/17* | (2019.01) |

(52) U.S. Cl.
CPC ............ *G06F 16/958* (2019.01); *G06F 8/36* (2013.01); *G06F 9/541* (2013.01); *G06F 9/547* (2013.01); *G06Q 30/0243* (2013.01); *A61B 5/165* (2013.01); *G06F 16/1734* (2019.01); *G06F 16/24* (2019.01); *G06Q 10/063* (2013.01)

(58) Field of Classification Search
CPC .... G06Q 30/0243; G06Q 10/063; G06F 8/36; G06F 16/958; G06F 9/547; G06F 9/541; G06F 16/24; G06F 16/1734; A61B 5/165
See application file for complete search history.

(56) References Cited

U.S. PATENT DOCUMENTS

| | | | |
|---|---|---|---|
| 2007/0061318 A1* | 3/2007 | Azizi | G06F 16/24 |
| 2011/0161319 A1* | 6/2011 | Chunilal | G06Q 30/0243 |
| | | | 707/733 |
| 2014/0201126 A1* | 7/2014 | Zadeh | A61B 5/165 |
| | | | 706/52 |
| 2017/0139891 A1* | 5/2017 | Ah-Soon | G06Q 10/063 |
| 2020/0372307 A1* | 11/2020 | Arun | G06F 9/541 |
| 2021/0049127 A1* | 2/2021 | Kunchakarra | G06F 16/1734 |

* cited by examiner

*Primary Examiner* — Tuan A Vu
(74) *Attorney, Agent, or Firm* — Buckley, Maschoff & Talwalkar LLC

(57) ABSTRACT

A report repository may store report results, and a web intelligence report server may include an SDK component to manage sessions, states, security, and resource access and to receive web intelligence data model authoring information, associated with a document, via an authoring API. The web intelligence report server may further include data sources associated with a plurality of data source types and data access associated with a plurality of data layers. A compound database platform of an in-memory database may create a report result via a data flow merge operation that combines multiple data sources into a single data source, based on the web intelligence data model authoring information, the data sources, and the data access. The report result may be stored in the report repository, and the web intelligence data model may be associated with a Web intelligence document as a data Source ("WaaS") reusable in other documents.

19 Claims, 14 Drawing Sheets

| WDM IDENTIFIER 1302 | DOCUMENT IDENTIFIER 1304 | AUTHORING AND CONSUMPTION INFORMATION 1306 | REPORT RESULT 1308 |
|---|---|---|---|
| WDM_101 | D_101 | | RR_101 |
| WDM_102 | D_102 | | RR_102 |

WEB INTELLIGENT DOCUMENT WAS A DATA SOURCE

BACKGROUND

A Web Intelligence ("WebI") Business Information ("BI") tool may provide several use cases (e.g., ad-hoc queries, analysis, and reporting). With the ad-hoc queries and analysis use cases, in each document the WebI may enable enrichments of metadata and data based on multiple data sources. It may, for example, create a virtual data source (e.g., a lightweight Extraction, Transformation, and Loading ("ETL") tool) that is only available inside the document. Users must then recreate these data preparations in each new document, which can be a time consuming and error-prone process.

To avoid this, it would be desirable to provide a Web intelligence document as a data Source ("WaaS") in a secure, automatic, and accurate manner.

SUMMARY

Methods and systems may be associated with web intelligence reports. A report repository may store report results, and a web intelligence report server may include an SDK component to manage sessions, states, security, and resource access and to receive web intelligence data model authoring information, associated with a document, via an authoring API. The web intelligence report server may further include data sources associated with a plurality of data source types and data access associated with a plurality of data layers. A compound database platform of an in-memory database may create a report result via a data flow merge operation that combines multiple data sources into a single data source, based on the web intelligence data model authoring information, the data sources, and the data access. The report result may be stored in the report repository, and the web intelligence data model may be associated with a Web intelligence document as a data Source ("WaaS") reusable in other documents.

Some embodiments comprise: means for receiving, at a Software Development Kit ("SDK") component of a web intelligence report server, web intelligence data model authoring information, associated with a document, via an authoring Application Programming Interface ("API"), wherein the SDK component is to manage sessions, states, security, and resource access; means for creating, by a compound database platform of an in-memory database, a report result via a data flow merge operation that combines multiple data sources into a single data source, based on the web intelligence data model authoring information, data sources associated with a plurality of data source types, and data access associated with a plurality of data layers; and means for storing the report result in a report repository, wherein the web intelligence data model is associated with a Web intelligence document as a data Source ("WaaS") reusable in other documents.

Some technical advantages of some embodiments disclosed herein are improved systems and methods to provide a Web intelligence document as a data Source ("WaaS") in a secure, automatic, and accurate manner.

BRIEF DESCRIPTION OF THE DRAWINGS

FIG. 13 illustrates a WDM database in accordance with some embodiments.

DETAILED DESCRIPTION

In the following detailed description, numerous specific details are set forth in order to provide a thorough understanding of embodiments. However, it will be understood by those of ordinary skill in the art that the embodiments may be practiced without these specific details. In other instances, well-known methods, procedures, components and circuits have not been described in detail so as not to obscure the embodiments.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Some embodiments described herein may be associated with an architecture where Web Intelligence ("WebI" consumes a WebI Data Model ("WDM"). As used herein, the term "WDM" may refer to a set of dimensions, measures, and/or detail objects gathered in a dictionary and managed by a model component. This may allow query foundation queries to be created on top of a model and processed by a query foundation layer (which may eventually drive how a WebI calculator computes results).

Some embodiments may let a user utilize WebI documents as a source. To do this, the system may let a user add new data providers based on another WebI document. In this way, the user can reuse all objects and enrichments created in the initial document. This new kind of data provider may be, for example, a specialization of Data Semantic Layer ("DSL") data sources that exposes WebI documents as if they were a universe.

Figure 1:
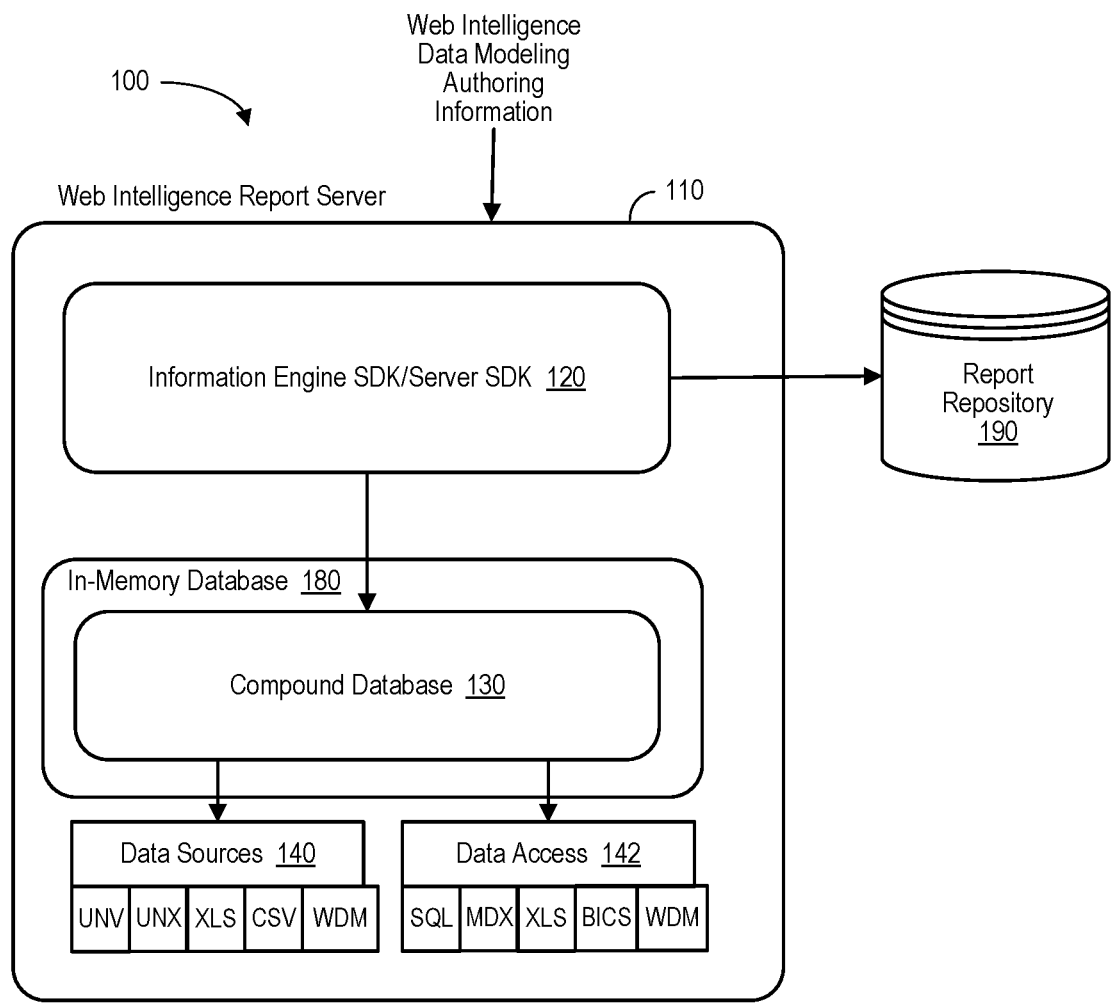
FIG. 1 is a high-level system in accordance with some embodiments.

Some embodiments may be associated with an extension of WebI report server capabilities. For example, FIG. 1 is a system 100 associated with WebI reports in accordance with some embodiments. The system 100 includes a repository 190 (e.g., a report repository) to store report results and a WebI report server 110, coupled to the repository 190, including a Software Development Kit ("SDK") component 120 that manages sessions, states, security, and resource access and receives WebI data model authoring information, associated with a document, via an authoring Application Programming Interface ("API"). The SDK component 120 might, for example, be associated with an information engine SDK or a Cadenza ("CDZ") server SDK.

The WebI report server 110 may also include data sources 140 associated with a plurality of data sources 140, such as universes ("UNV" or "UNX"), Excel Files ("XLS"), Comma Separated Values ("CSV"), etc. Similarly, the WebI report server 110 may include data access 142 associated with a plurality of data layers, such as Structured Query Language ("SQL"), Multi-Dimensional Expressions ("MDX"), Excel ("XLS"), Business Information Consumer Services ("BICS"), etc.

According to some embodiments, a compound database platform 130 of an in-memory database 180 may be coupled to the SDK component 120, data sources 140, and data access 142. The compound database platform 130 may, in some embodiments, create a report result via a data flow merge operation that combines multiple data sources into a single data source, based on the web intelligence data model authoring information, the data sources 140, and the data access 142. The report result may then be stored in the report repository 190, and the WDM may be associated with a WebI document as a data Source ("WaaS") reusable in other documents.

As used herein, devices, including those associated with the system 100 and any other device described herein, may exchange information via any communication network which may be one or more of a Local Area Network ("LAN"), a Metropolitan Area Network ("MAN"), a Wide Area Network ("WAN"), a proprietary network, a Public Switched Telephone Network ("PSTN"), a Wireless Application Protocol ("WAP") network, a Bluetooth network, a wireless LAN network, and/or an Internet Protocol ("IP") network such as the Internet, an intranet, or an extranet. Note that any devices described herein may communicate via one or more such communication networks.

The system 100 may store information into and/or retrieve information from various data stores, such as the repository 190, which may be locally stored or reside remote from the WebI report server 110. Although a single WebI report server 110 and compound database 130 are shown in FIG. 1, any number of such devices may be included. Moreover, various devices described herein might be combined according to embodiments of the present invention. For example, in some embodiments, the WebI report server 110 and repository 190 might comprise a single apparatus. The system 100 functions may be performed by a constellation of networked apparatuses, such as in a distributed processing or cloud-based architecture.

A user may access the system 100 via a remote device (e.g., a Personal Computer ("PC"), tablet, or smartphone) to view information about and/or manage operational information in accordance with any of the embodiments described herein. In some cases, an interactive graphical user interface display may let an operator or administrator define and/or adjust certain parameters (e.g., to implement various rules and policies) and/or provide or receive automatically generated recommendations or results from the system 100.

Figure 2:
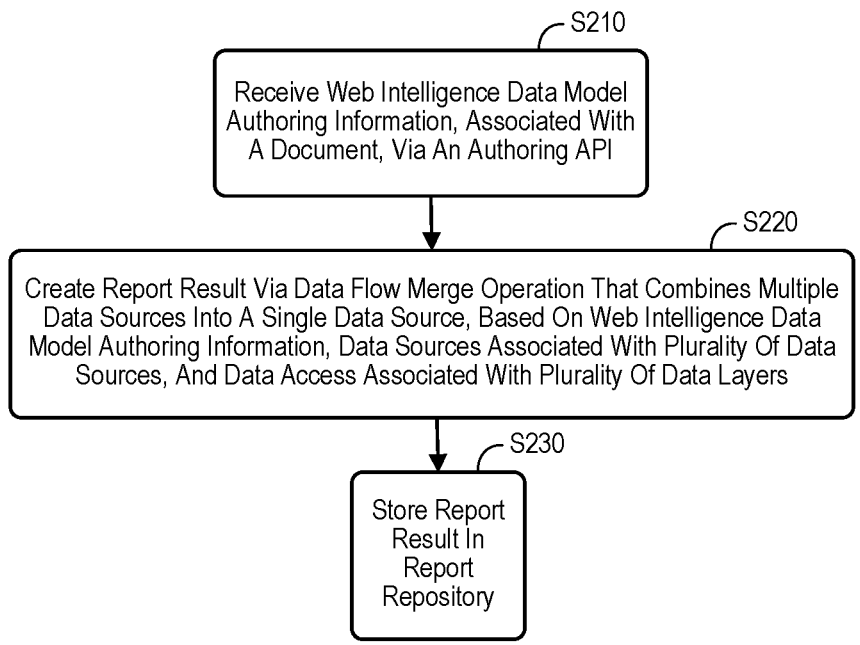
FIG. 2 is a method according to some embodiments.

FIG. 2 is a method that might performed by some or all of the elements of any embodiment described herein. The flow charts described herein do not imply a fixed order to the steps, and embodiments of the present invention may be practiced in any order that is practicable. Note that any of the methods described herein may be performed by hardware, software, an automated script of commands, or any combination of these approaches. For example, a computer-readable storage medium may store thereon instructions that when executed by a machine result in performance according to any of the embodiments described herein.

At S210, web intelligence data model authoring information, associated with a document, may be received via an authoring Application Programming Interface ("API"). The authoring information may be received, for example, at a Software Development Kit ("SDK") component of a web intelligence report server. The SDK component may, according to some embodiments, manage sessions, states, security, and resource access for the system.

At S220, the system may create a report result via a data flow merge operation that combines multiple data sources into a single data source, based on the web intelligence data model authoring information, data sources associated with a plurality of data source types, and data access associated with a plurality of data layers. The data flow merge operation might, for example, be associated with a compound database platform of an in-memory database. At S230, the report result may be stored in a report repository. Note that the web intelligence data model may be associated with a Web intelligence document as a data Source ("WaaS") that is reusable in other documents.

Figure 3:
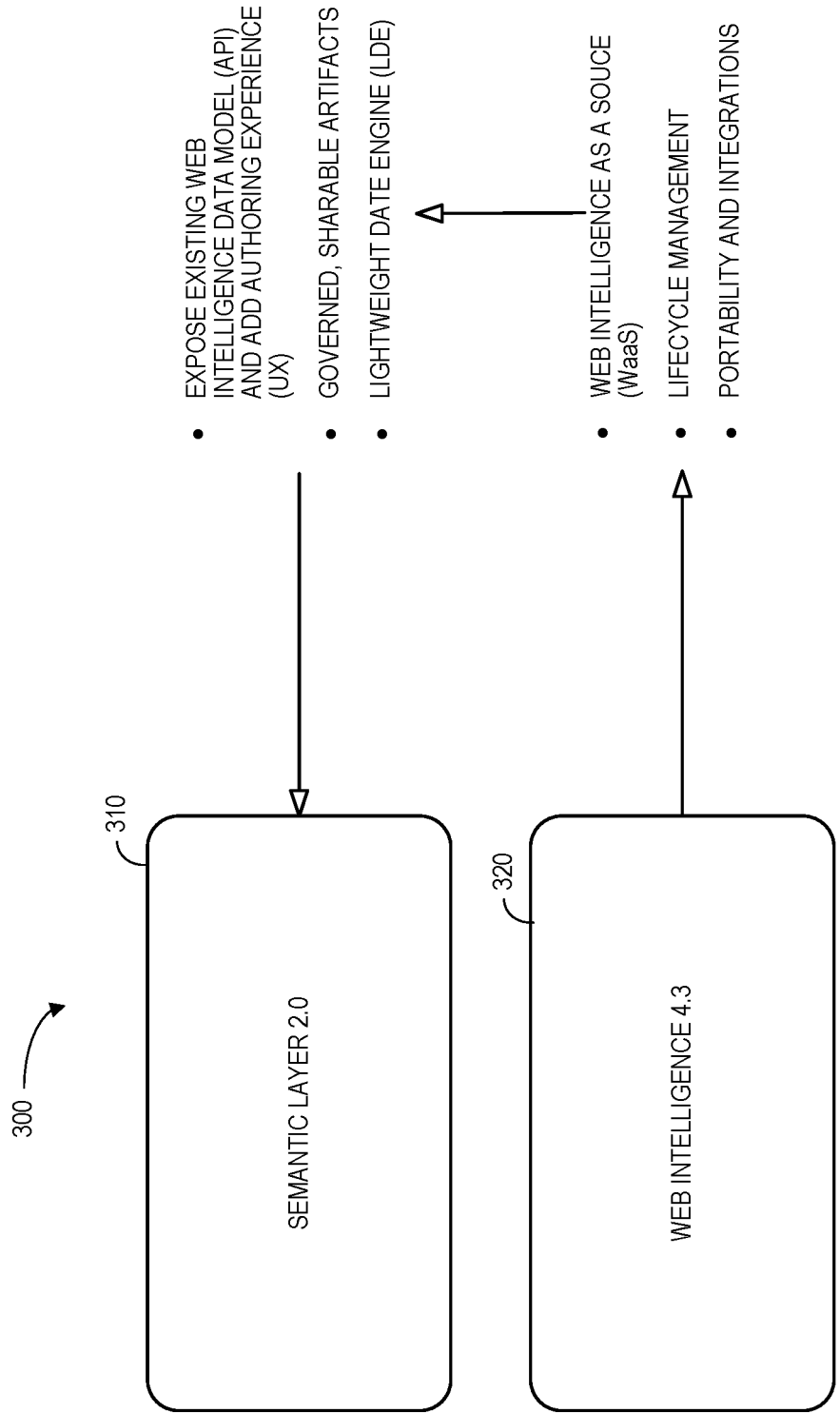
FIG. 3 is a business object explorer information flow in accordance with some embodiments.

FIG. 3 is a business object explorer information flow 300 in accordance with some embodiments. The information flow 300 may include a semantic layer 310, such as semantic layer 2.0 from SAP®, that comprises an abstract representation of business entities (dimensions, measures, etc.) enriched with semantics closely related to the business terms such that a mapping is done between the deep entities and the business terms. The semantic layer 310 might, according to some embodiments:
    connect to many data sources (and be agnostic to data sources),
    empower business users with the autonomy needed to access, analyze, enrich and/or share information freely and securely using familiar business terms,
    provide a common user experience, best access method for each specific data source, and access to various data sources for all front ends,
    model data in a "shared object model,"
    etc.

The information flow 300 may also include a WebI 320, such as Web 4.3 from SAP®. The WebI 320 may, for example, provide WaaS, lifecycle management, portability and integrations, etc. These, in turn may flow to expose a WDM (API) and add an authoring experience ("UX"), governed sharable artifacts, a Lightweight Data Engine ("LDE"), etc. for the semantic layer 310.

Figure 4:
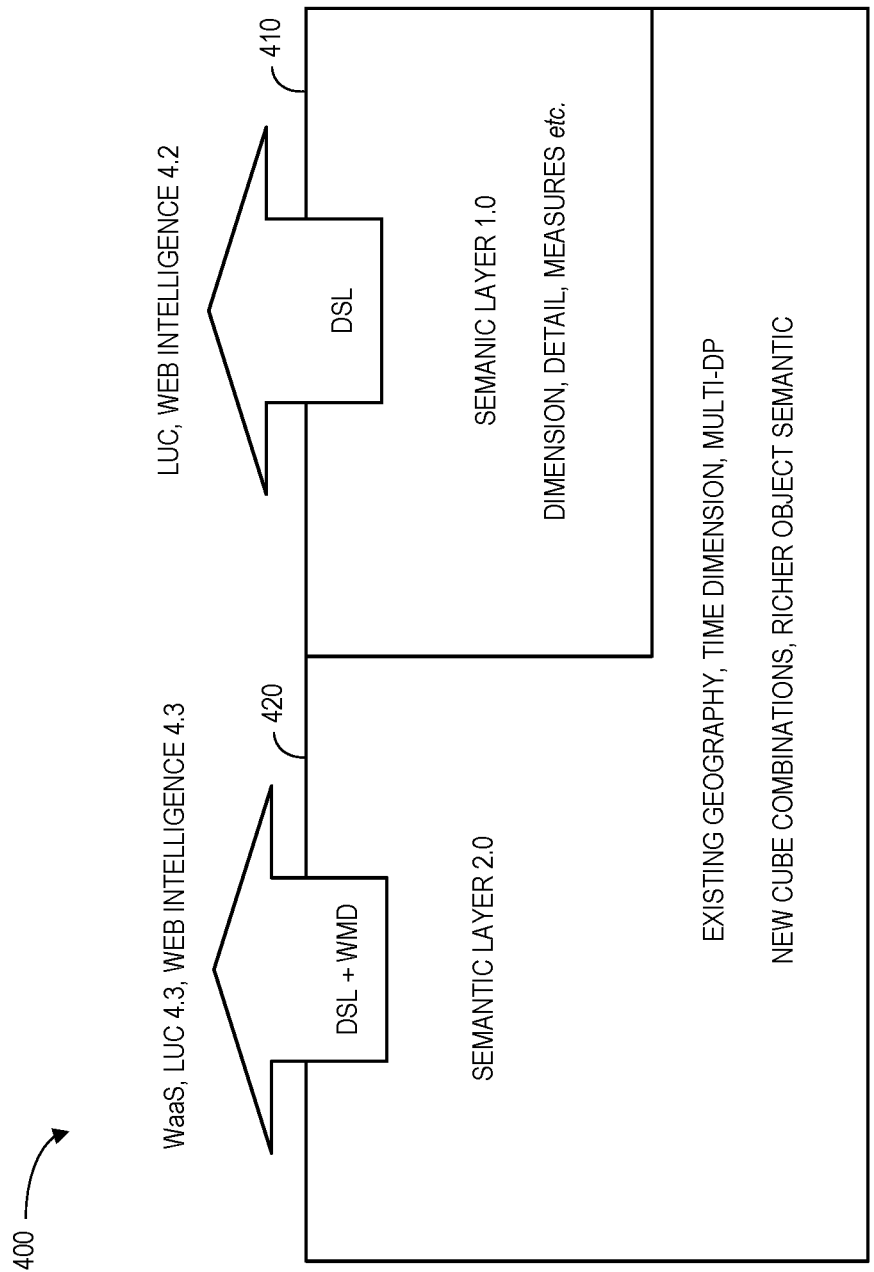
FIG. 4. Is a view of semantic layer implementations according to some embodiments.

FIG. 4. Is a view 400 of semantic layer implementations according to some embodiments. As shown in FIG. 4, a semantic layer 1.0 410 (e.g., dimensions, details, measures, etc.) may use DSL to communication with Live Universe Connectivity ("LUC") and/or WebI 4.2. A semantic layer 2.0 420 (e.g., providing existing geography, time dimension, multiple Data Providers ("multi-DP"), new cube combinations, richer object semantics, etc.) may use DSL and/or WMD to communicate with WaaS, LUC, WebI 4.3, etc.

Figure 5:
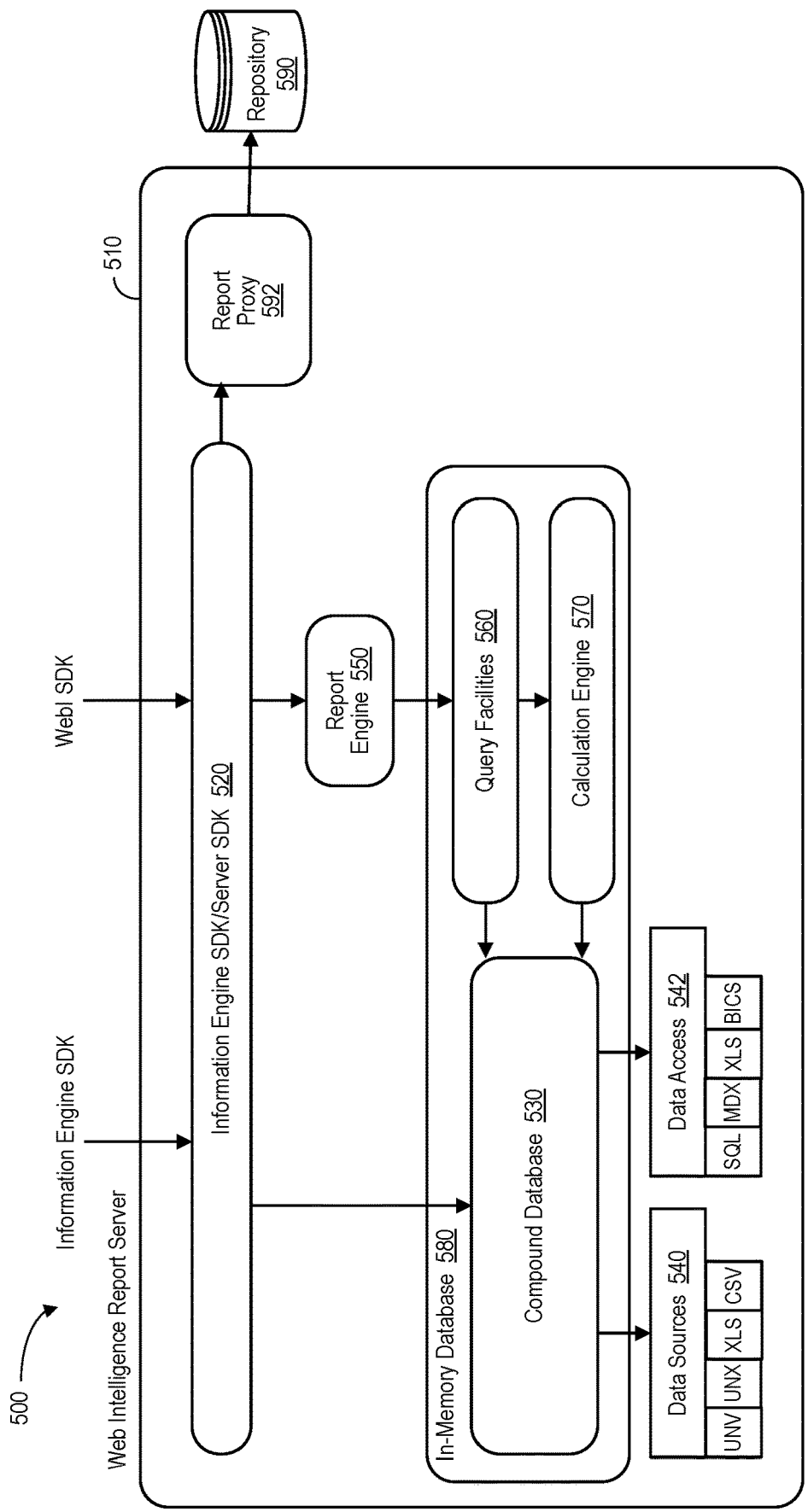
FIG. 5 is a more detailed system diagram in accordance with some embodiments.

FIG. 5 is a more detailed system 500 diagram in accordance with some embodiments. The system 100 includes a WebI report server 510 that stores information into a repository 590 (e.g., a report repository) via a repository proxy 592 (e.g., associated with a Business Objects Enterprise ("BOE") connection). The WebI report server 510, which may be associated with the Common Object Request Broker Architecture ("CORBA"), includes a WebI information engine SDK 520 that may manage sessions and states, manage security, manage resources access (thru the repot proxy 592), audit functionality, etc. An information engine SDK API may, for example, manage calls for a compound database component 530 while a CDZ server SDK API manages calls for reporting needs (e.g., to redirect to a report engine 550).

The compound database 530 may be associated with an in-memory database 580 and manage and store all data and metadata available and have an API to create/update/delete a data provider, create/update/delete a user object, get a document dictionary (all objects available), refresh data providers, etc. The compound database 530 storage may contain, for example, a data providers definition (a data provider is defined by a query on a data source). The compound database 530 may also provide a local storage for data flows provided by a query execution. Moreover, user objects (additional metadata definition) might include variables, synchronized dimensions, grouping, geographic enrichments, time enrichments, etc.

Data sources 540 may provide an abstract layer with a specific implementation for each type of data source (UNV, UNX, XLS, FreeHand SQL, etc.), create queries, and generate an executable statement. A data sources 540 API may be associated with query generation to provide data source metadata (all available objects), provide a List Of Values ("LOVs") for objects, allow parameters resolution (variables/prompts), provide an executable query statement for an associated data access 542 layer, etc. The data access 542 may comprise an abstract layer with a specific implementation for each type of data layer (SQL, BICS, MDX, XLS files, etc.) and/or provide an executable query statement and return result dataflows. The data access 542 might be associated with an API, query execution, describe results, iterate on results, etc.

The report engine 550 may generate paginated reports in different formats (e.g., XLS, PDF, text, etc.). An API of the report engine 550 may update a report structure and get pages. The report engine 550 storage may contain a report specification (defines all reports definition). The report server 510 may further include query facilities 560 to provide API according a client's needs to perform queries on top of the compound database 530, check queries integrity (use only objects available existing in compound database 530 dictionary), translate a client's request in a "calculator" internal language, and provide iterator on a query result. APIs available in connection with the query facilities 560 may include a custom API for report engine 550 needs (e.g., to define several queries (one query/bloc in the report), retrieve results with a random access) and a custom API for analytics needs (e.g., a simple API to define a query and retrieve results as an array). Uses of the query facilities 560 may include metadata provided by compound database 530 dictionary.

The report server 510 may further include a calculation engine 570 to execute calculation plans on top of data stored in compound database 530. An API associated with the calculation engine 570 may comprise a custom API dedicated for query facilities 560 (e.g., to allow for the creation, optimization, and/or execution of calculation plans). The calculation engine 570 may be used for dataflows provided by compound database 530 (e.g., roots for calculation plan).

Figure 6:
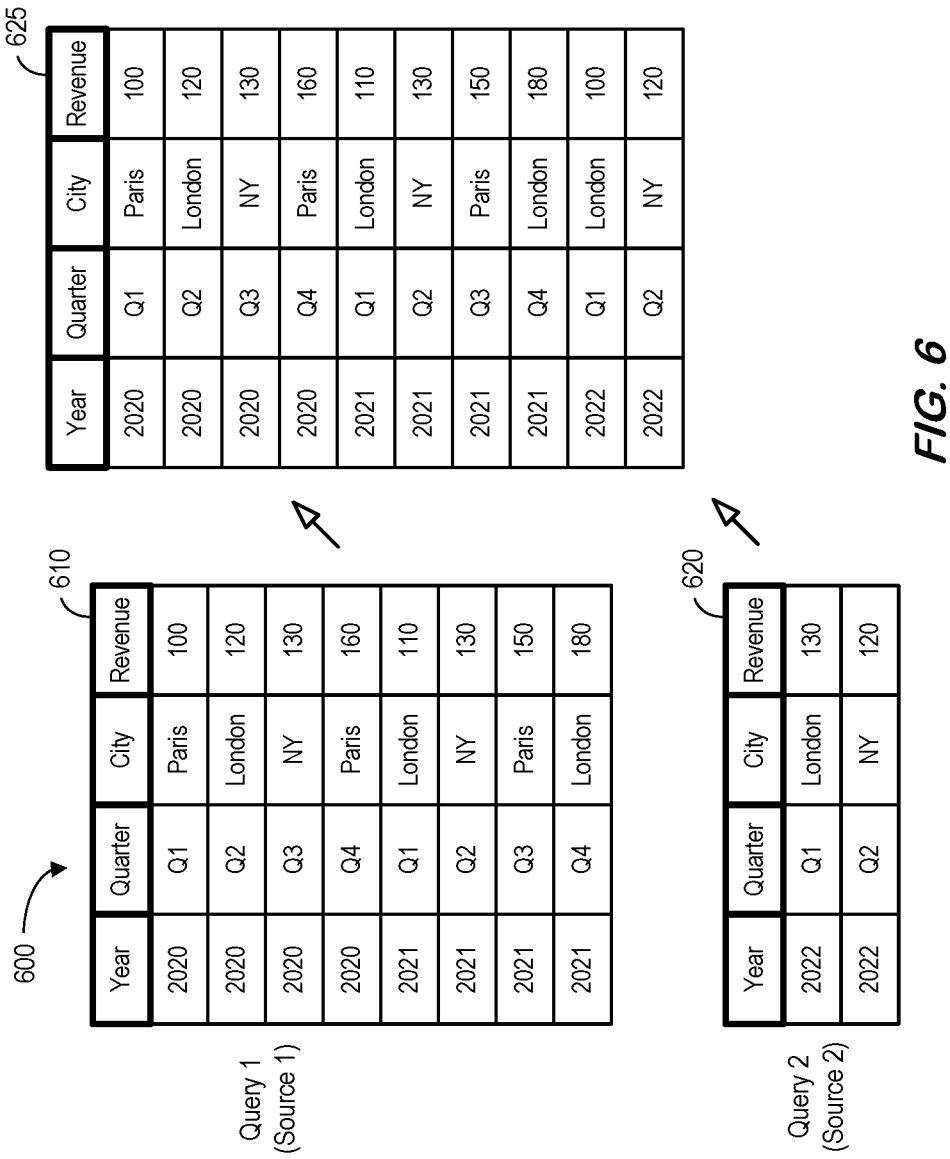
FIG. 6 shows a combination of information from multiple data sources according to some embodiments.
Figure 7:
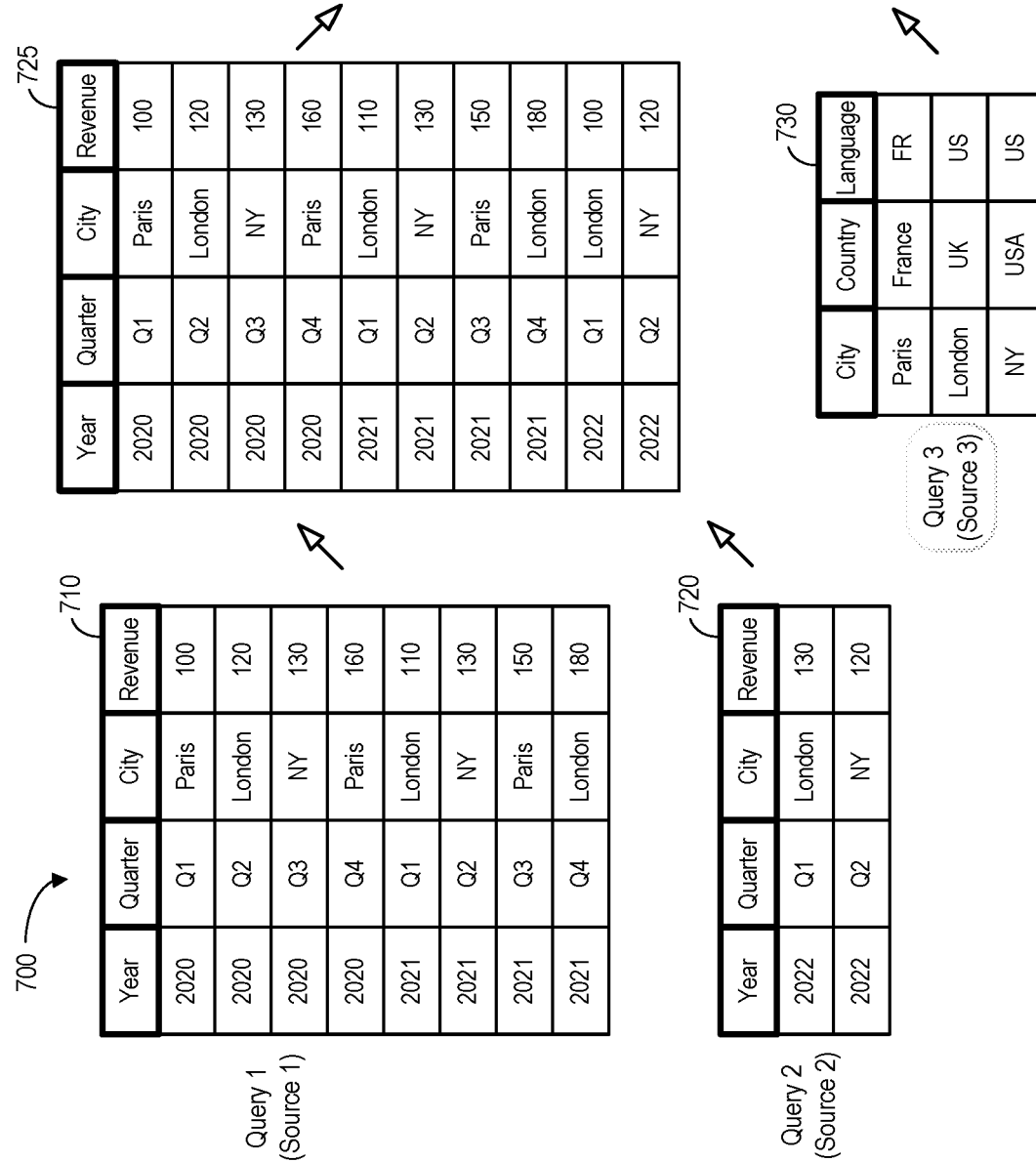
FIG. 7 shows the addition of a third data source in accordance with some embodiments.
Figure 8:
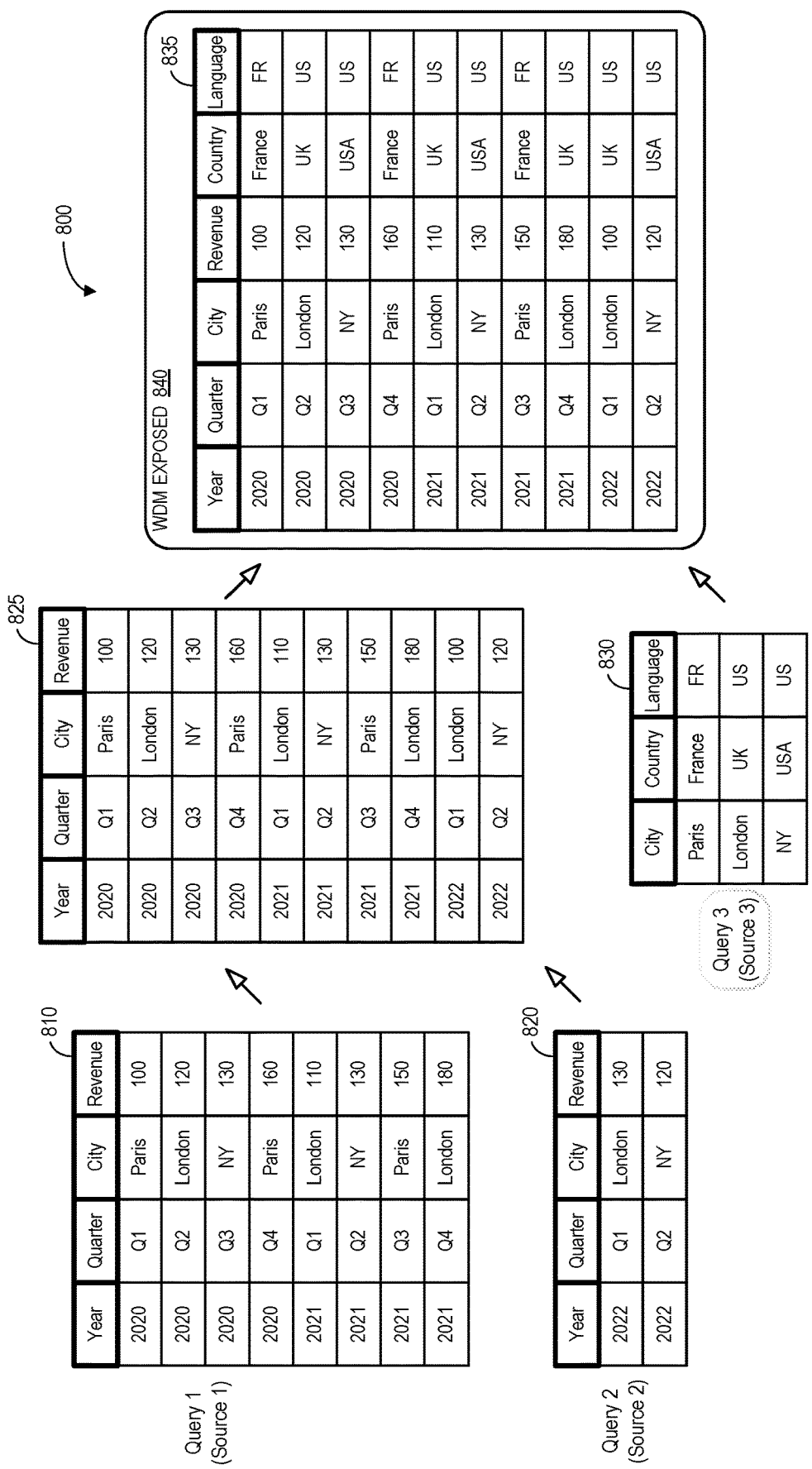
FIG. 8 shows an exposed web intelligence data model according to some embodiments.

FIG. 6 shows 600 a combination of information from multiple data sources according to some embodiments. A first source 610 includes year, quarter, city, and revenue values for the years 2020 and 2021. A second source 620 includes year, quarter, city, and revenue values for the year 2022. The system may combine these sources of information 610, 620 into a single data source result 625 (including information for years 2020 through 2022) for easier consumption. FIG. 7 shows 700 the addition of a third data source 730 in accordance with some embodiments. As before, the first data source 710 and second data source 720 were combined to create a single data source result 725. Next, the third data source 730 (including city, country, and language) is combined with the single data source result 725. FIG. 8 shows 800 an exposed WDM 840 according to some embodiments. Again, the first data source 810 and second data source 820 are combined to create a single data source result 825. Next, the third data source 830 (including city, country, and language) is combined with the single data source result 825. The new single data source result 835 (including year, quarter, city, revenue, country, and language for years 2020 through 2022) are stored in the exposed WDM 840.

Figure 9:
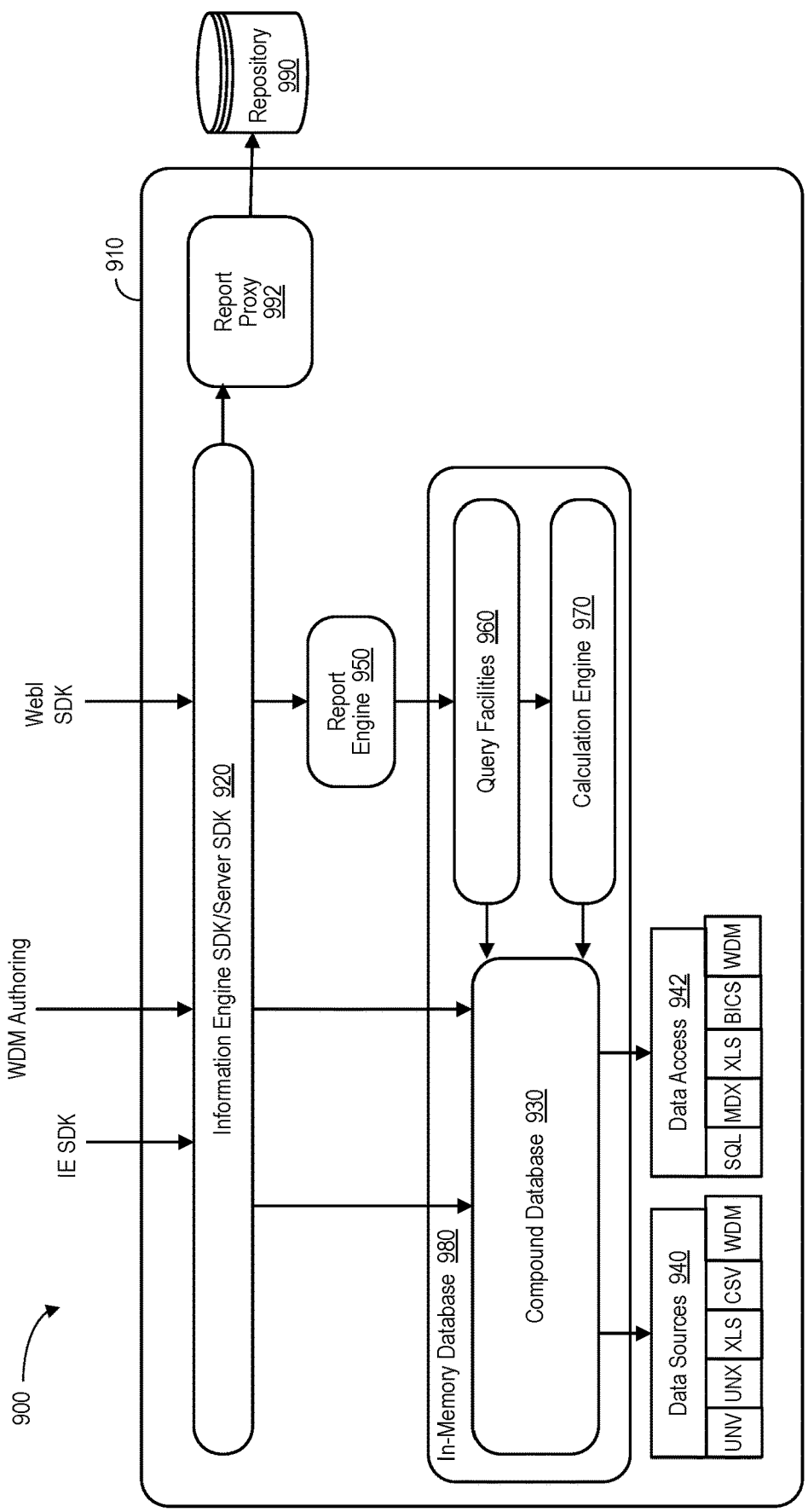
FIG. 9 is a system with an authoring API in accordance with some embodiments.

FIG. 9 is a system 900 with a WDM authoring API in accordance with some embodiments. As before, a WebI report server 910 may store report results into a repository 990 (via a report proxy 992 that may be associated with a BOE connection). An SDK 920 may also send information to a compound database 930 (associated with an in-memory database 980) and a report engine 950. The report engine 950 may use query facilities 960 and a calculation engine 970 to access data sources 940 and data access 942 via the compound database 930.

In this embodiment, the system 900 may further receive WDM authoring information. In particular, the SDK 920 of the WebI report server 910 may receive the WDM authoring information and forward it to the compound database 930. In this way, a WDM may expose the existing WebI data model (API) in memory database as any other data source, hiding multi-source complexity from consumers.

Figure 10:
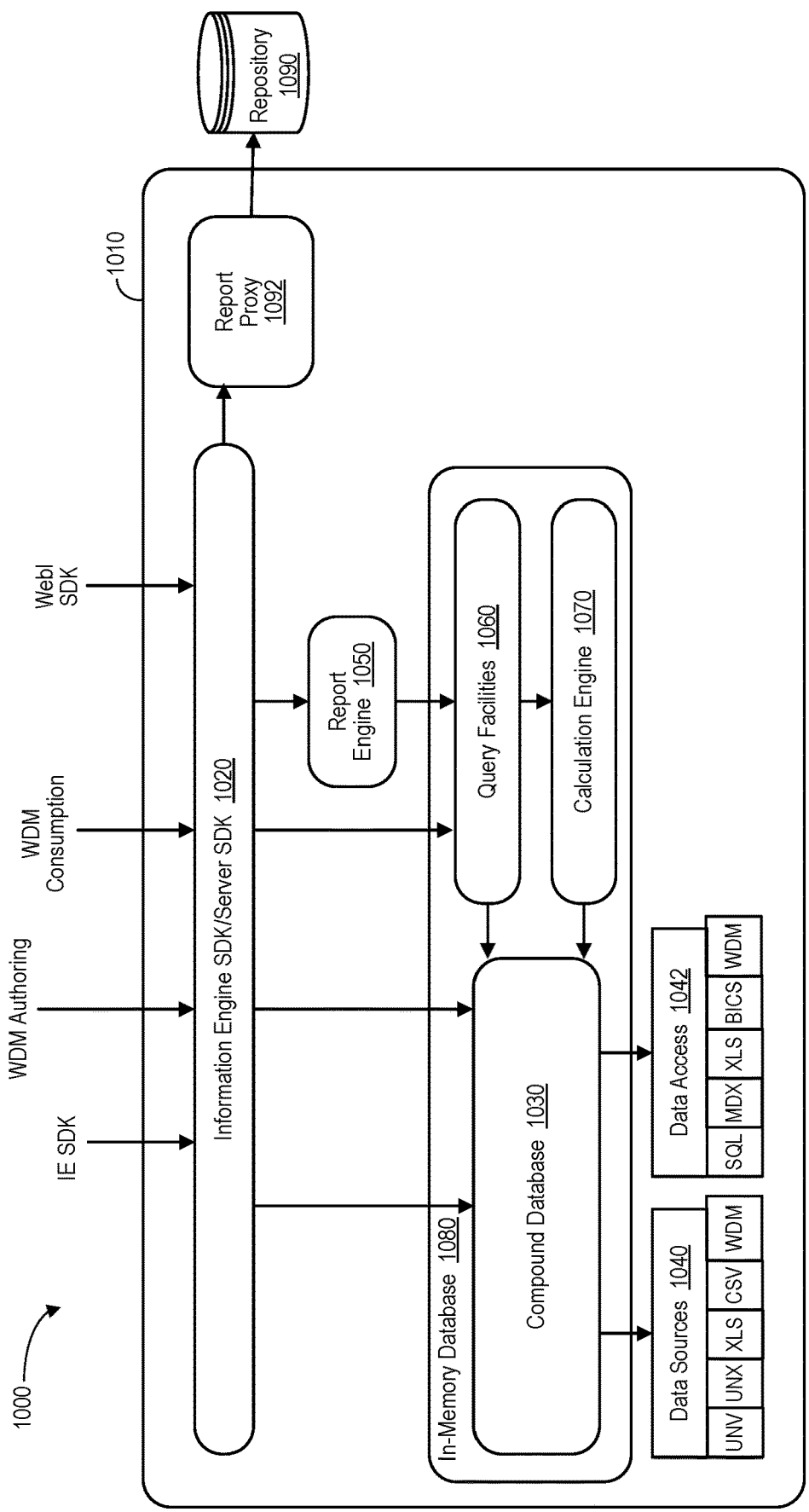
FIG. 10 is a system with a consumption API according to some embodiments.

FIG. 10 is a system 1000 with a WDM consumption API according to some embodiments. As before, a WebI report server 1010 may store report results into a repository 1090 (via a report proxy 1092 that may be associated with a BOE connection). An SDK 1020 may also send information to a compound database 1030 (associated with an in-memory database 1080) and a report engine 1050. The report engine 1050 may use query facilities 1060 and a calculation engine 1070 to access data sources 1040 and data access 1042 via the compound database 1030.

In this embodiment, the system 1000 may further receive WDM consumption information (e.g., a query language). In particular, the SDK 1020 of the WebI report server 1010 may receive the WDM consumption information and forward it to the query facilities 1060 (e.g., via a WDM plugin). In this way, the system 1000 may create a report result via a data flow merge operation that combines multiple data sources into a single data source, based on the WDM authoring and consumption information, the data sources 1040, and the data access 1042. The report result may be stored in the report repository 1090, and the WDM may be associated with a WaaS reusable in other documents.

Figure 11:
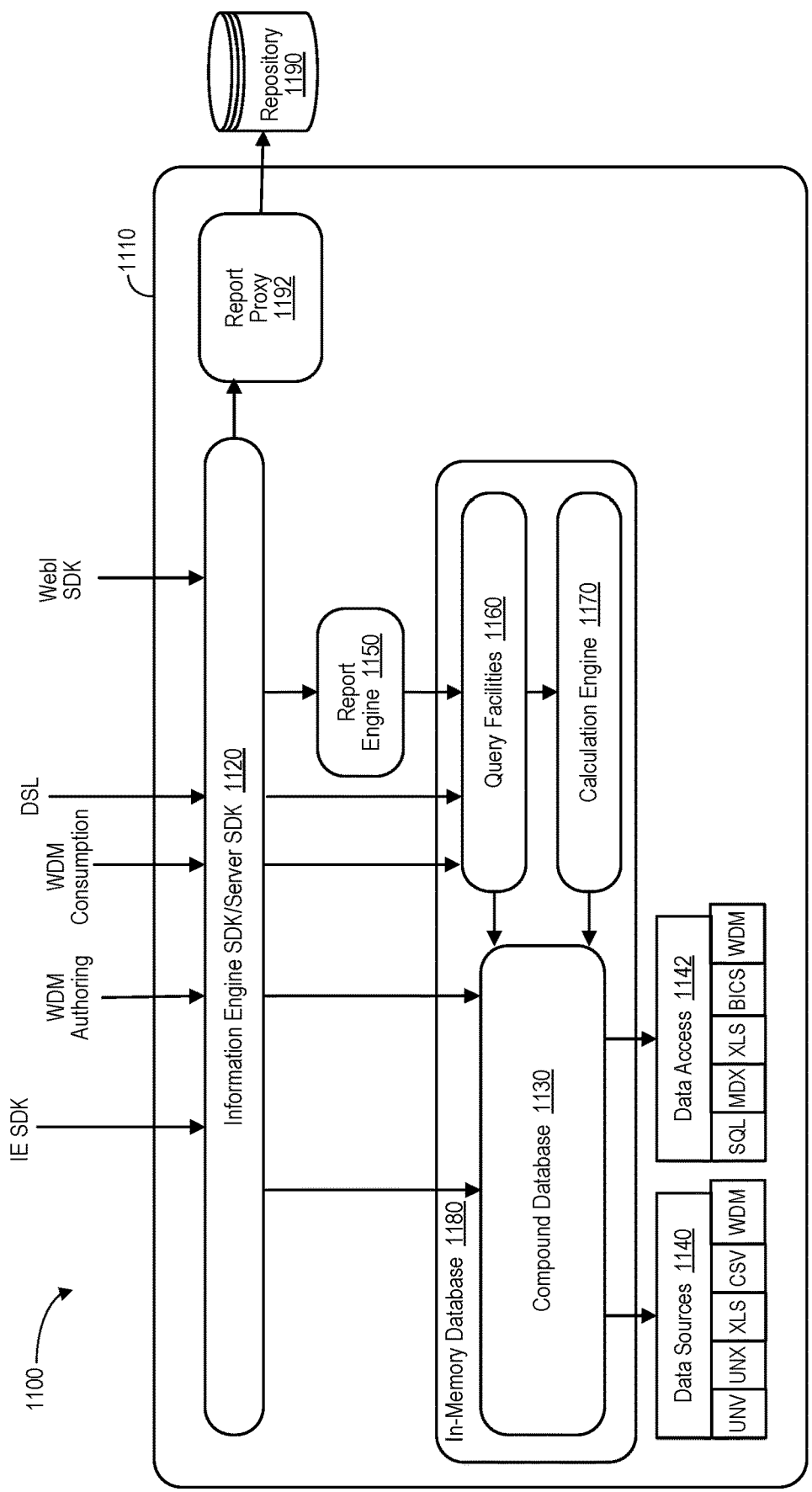
FIG. 11 is another system with a consumption API in accordance with some embodiments.

FIG. 11 is another system 1100 with a consumption API in accordance with some embodiments. Again, a WebI report server 1110 may store report results into a repository 1190 (via a report proxy 1192 that may be associated with a BOE connection). An SDK 1120 may also send information to a compound database 1130 (associated with an in-memory database 1180) and a report engine 1150. The report engine 1150 may use query facilities 1160 and a calculation engine 1170 to access data sources 1140 and data access 1142 via the compound database 1130.

In this embodiment, the system 1100 may further receive DSL consumption information (e.g., another way to access and consume the WDM data). In particular, the SDK 1120 of the WebI report server 1110 may receive the DSL consumption information and forward it to the query facilities 1160 (e.g., via a data semantics layer plugin). In this way, the system 1100 may create a report result via a data flow merge operation that combines multiple data sources into a single data source, based on the WDM authoring and consumption information, the data sources 1140, and the data access 1142. The report result may be stored in the report repository 1190, and the WDM may be associated with a WaaS reusable in other documents.

As previously described a WebI BI tool may provide several use cases (e.g., ad-hoc queries, analysis, and reporting). With the ad-hoc queries and analysis use cases, in each document the WebI may enable enrichments of metadata and data based on multiple data sources. It may, for example, create a virtual data source (e.g., a lightweight ETL) that only available inside the document. Users must then recreate these data preparations in each new document, which can be a time consuming and error-prone process. An advantage of WaaS may be that it lets a user reuse this data preparation as a source for any new document (and then focus on the analysis and reporting use cases). According to some embodiments, this WebI data source may be consumed as a universe (e.g., associated with a BOE semantic layer) and any products supporting universes. This WebI data source can be also seen as a semantic layer extended by business users and, for business users (e.g., of semantic layer 2.0), be compared to a universe dedicated for Information Technology ("IT") users. Embodiments may also allow a shared data preparation for business users. Embodiments may comprise a simplification of multi-source consumption and instead provide a single virtual data provider (e.g., a lightweight and/or self-service ETL).

Figure 12:
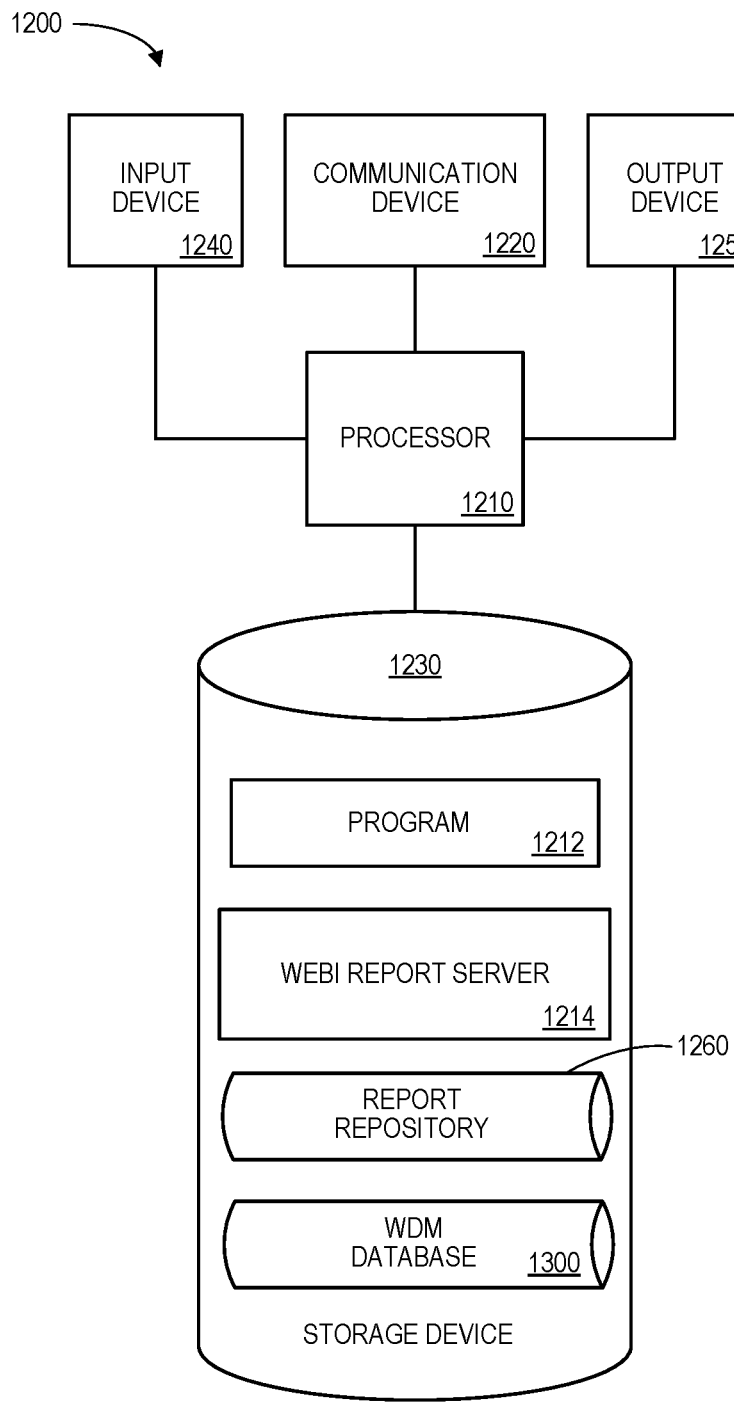
FIG. 12 is an apparatus or platform according to some embodiments.

Note that the embodiments described herein may be implemented using any number of different hardware configurations. For example, FIG. 12 is a block diagram of an apparatus or platform 1200 that may be, for example, associated with the system 100 of FIG. 1 (and/or any other system described herein). The platform 1200 comprises a processor 1210, such as one or more commercially available CPUs in the form of one-chip microprocessors, coupled to a communication device 1260 configured to communicate via a communication network (not shown in FIG. 12). The communication device 1260 may be used to communicate, for example, with one or more remote user platforms, cloud resource providers, etc. The platform 1200 further includes an input device 1240 (e.g., a computer mouse and/or keyboard to input rules or logic) and/an output device 1250 (e.g., a computer monitor to render a display, transmit recommendations, and/or create reports). According to some embodiments, a mobile device and/or PC may be used to exchange information with the platform 1200.

The processor 1210 also communicates with a storage device 1230. The storage device 1230 can be implemented as a single database or the different components of the storage device 1230 can be distributed using multiple databases (that is, different deployment information storage options are possible). The storage device 1230 may comprise any appropriate information storage device, including combinations of magnetic storage devices (e.g., a hard disk drive), optical storage devices, mobile telephones, and/or semiconductor memory devices. The storage device 1230 stores a program 1212 and/or WebI report server 1214 for controlling the processor 1210. The processor 1210 performs instructions of the programs 1212, 1214, and thereby operates in accordance with any of the embodiments described herein. For example, the processor 1210 may store report results in a report repository, and a web intelligence report server may include an SDK component to manage sessions, states, security, and resource access and to receive web intelligence data model authoring information, associated with a document, via an authoring API. The web intelligence report server may further include data sources associated with a plurality of data source types and data access associated with a plurality of data layers. The processor 1210 may create a report result via a data flow merge operation that combines multiple data sources into a single data source, based on the web intelligence data model authoring information, the data sources, and the data access. The report result may be stored in a report repository 1260, and the WDM may be associated with a WaaS reusable in other documents.

The programs 1212, 1214 may be stored in a compressed, uncompiled and/or encrypted format. The programs 1212, 1214 may furthermore include other program elements, such as an operating system, clipboard application, a database management system, and/or device drivers used by the processor 1210 to interface with peripheral devices.

As used herein, information may be "received" by or "transmitted" to, for example: (i) the platform 1200 from another device; or (ii) a software application or module within the platform 1200 from another software application, module, or any other source.

In some embodiments (such as the one shown in FIG. 12), the storage device 1230 further stores the report repository 1260 and a WDM database 1300. An example of a database that may be used in connection with the platform 1200 will now be described in detail with respect to FIG. 13. Note that the database described herein is only one example, and additional and/or different information may be stored therein. Moreover, various databases might be split or combined in accordance with any of the embodiments described herein.

Referring to FIG. 13, a table is shown that represents the WDM database 1300 that may be stored at the platform 1200 according to some embodiments. The table may include, for example, entries associated with exposed WebI data models. The table may also define fields 1302, 1304, 1306, 1308, for each of the entries. The fields 1302, 1304, 1306, 1308 may, according to some embodiments, specify: a WDM identifier 1302, a document identifier 1304, authoring and consumption information 1306, and a report result 1308. The WDM database 1300 may be created and updated, for example, when new WDMs are authored or consumed for documents. According to some embodiments, the WDM database 1300 may further store details about users, data sources, data access, etc.

The WDM identifier 1302 might be a unique alphanumeric label or link that is associated with a particular WDM (e.g., in connection with document identifier 1304). The authoring and consumption information 1306 may define how the WDM is constructed and/or accessed by a user. The report result 1308 may contain the information accessed via the WDM (and point to a file in a report repository).

Thus, embodiments may provide a WaaS in a secure, automatic, and accurate manner. Some embodiments may provide reusability of any enrichment done on a WebI document (e.g., multi-source, calculations, etc.). Embodiments may reduce the load on physical databases because the data is already cached in the WebI document source. This means that a scheduled source document may be refreshed once, and then all document based on that WebI source document will benefit from the source document cache. This WebI data source may be consumed as a universe (e.g., associated with the a BOE semantic layer) and by any products that support universes.

The following illustrates various additional embodiments of the invention. These do not constitute a definition of all possible embodiments, and those skilled in the art will understand that the present invention is applicable to many other embodiments. Further, although the following embodiments are briefly described for clarity, those skilled in the art will understand how to make any changes, if necessary, to the above-described apparatus and methods to accommodate these and other embodiments and applications.

Figure 14:
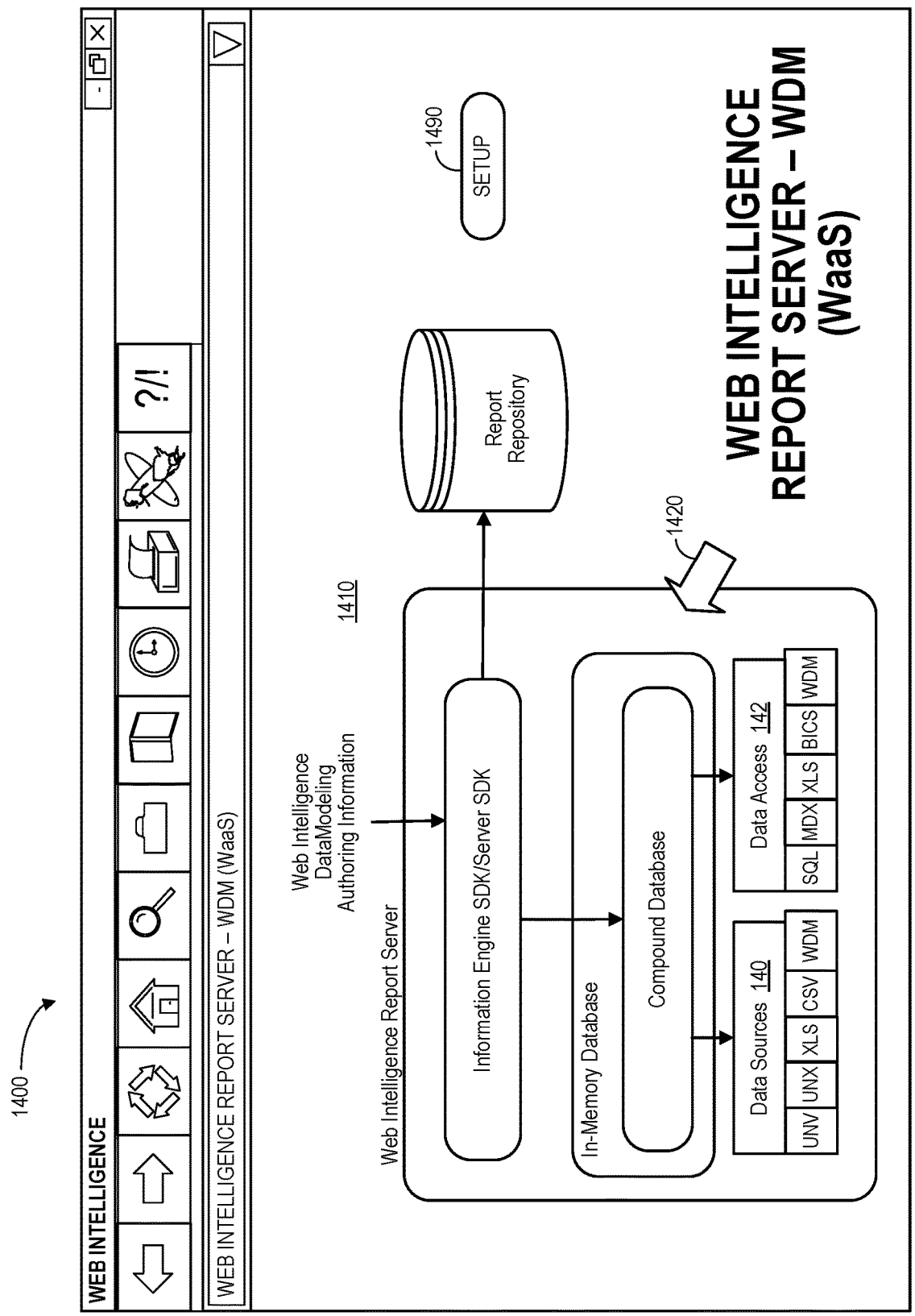
FIG. 14 is a WebI report server display associated with WaaS according to some embodiments.

Although specific hardware and data configurations have been described herein, note that any number of other configurations may be provided in accordance with some embodiments of the present invention (e.g., some of the information associated with the databases described herein may be combined or stored in external systems). Moreover, although some embodiments are focused on particular types of applications and services, any of the embodiments described herein could be applied to other types of applications and services. In addition, any displays shown herein are provided only as examples, and other types of user interface could be implemented. For example, FIG. 14 is a human machine interface display 1400 according to some embodiments. The display 1400 includes a graphical representation 1410 of elements of a WebI report server associated with WaaS according to some embodiments. Selection of an element (e.g., via a touchscreen or computer pointer 1420) may result in display of a pop-up window containing various options (e.g., to adjust rules or logic, assign various machine or devices, etc.). The display 1400 may also include a user-selectable "Setup" icon 1490 (e.g., to configure parameters for WaaS as described with respect any of the embodiments described herein).

The present invention has been described in terms of several embodiments solely for the purpose of illustration. Persons skilled in the art will recognize from this description that the invention is not limited to the embodiments described but may be practiced with modifications and alterations limited only by the spirit and scope of the appended claims.

The invention claimed is:

1. A system associated with web intelligence reports, comprising:
 a report repository to store report results; and
 a web intelligence report server, coupled to the report repository, including:
  a Software Development Kit ("SDK") component to manage sessions, states, security, and resource access and to receive web intelligence data model authoring information, associated with a document, via an authoring Application Programming Interface ("API"),
  data sources associated with a plurality of data source types,
  data access associated with a plurality of data layers, and
  a compound database platform of an in-memory database, coupled to the SDK component, data sources, and data access, including:
   a computer processor, and
   a memory storage device coupled to the computer processor and including instructions that, when executed by the computer processor, enable the compound database platform to:
    (i) create a report result via a data flow merge operation that combines multiple data sources into a single data source, based on the web intelligence data model authoring information, the data sources, and the data access,
  query facilities to receive web intelligence data model consumption information from a report engine and transmit a get metadata message to the compound database platform, and
  a calculation engine to execute calculation plans on top of data stored in compound database platform, wherein the calculation receives web intelligence data model consumption information from the query facilities and transmits a get data message to the compound database platform;
 wherein the report result is stored in the report repository and the web intelligence data model is associated with a Web intelligence document as a data Source ("WaaS") reusable in other documents.

2. The system of claim 1, wherein the SDK component is further to receive web intelligence data model consumption information via a consumption API, and the compound database is further to access a web intelligence data model via the data sources and data access.

3. The system of claim 2, wherein the web intelligence report server further includes:
 the report engine, to generate paginated reports in different formats, that receives web intelligence data model consumption information from the SDK component.

4. The system of claim 3, wherein the
 query facilities check query integrity, translate requests in an internal language, and provide an iterator on query result and the get metadata and get data messages comprise read only messages.

5. The system of claim 1, wherein the compound database platform further performs data acquisition and creates a custom metadata layer.

6. The system of claim 1, wherein the compound database platform contains at least one of: (i) a data provider definition, (ii) local storage for data flows provided by query execution, (iii) user objects with additional metadata definition, (iv) variables, (v) synchronized dimensions, (vi) grouping, (vii) geographic enrichments, and (viii) time enrichments.

7. The system of claim 1, wherein each data source is associated with an abstract layer with a specific implementation to create queries and generate an executable statement.

8. The system of claim 1, wherein the data access is associated with an abstract layer with a specific implementation for each data layer to execute a query statement and return result dataflows.

9. The system of claim 1, wherein the SDK component is further to receive information engine and web intelligence SDK data.

10. A computer-implemented method associated with web intelligence reports, comprising:

receiving, at a Software Development Kit ("SDK") component of a web intelligence report server, web intelligence data model authoring information, associated with a document, via an authoring Application Programming Interface ("API"), wherein the SDK component is to manage sessions, states, security, and resource access;

creating, by a compound database platform of an in-memory database, a report result via a data flow merge operation that combines multiple data sources into a single data source, based on the web intelligence data model authoring information, data sources associated with a plurality of data source types, and data access associated with a plurality of data layers;

storing the report result in a report repository;

receiving, by query facilities, web intelligence data model consumption information from a report engine and transmitting a get metadata message to the compound database platform; and executing, by a calculation engine, calculation plans on top of data stored in compound database platform, wherein the calculation receives web intelligence data model consumption information from the query facilities and transmits a get data message to the compound database platform, wherein the web intelligence data model is associated with a Web intelligence document as a data Source ("WaaS") reusable in other documents.

11. The method of claim 10, wherein the SDK component is further to receive web intelligence data model consumption information via a consumption API, and the compound database is further to access a web intelligence data model via the data sources and data access.

12. The method of claim 11, wherein the web intelligence report server further includes:

the report engine, to generate paginated reports in different formats, that receives web intelligence data model consumption information from the SDK component.

13. The method of claim 12, wherein the query facilities check query integrity, translate requests in an internal language, and provide an iterator on query result and the get metadata and get data messages comprise read only messages.

14. A non-transitory, computer readable medium having executable instructions stored therein that, when executed by a computer processor cause the processor to perform a method associated with web intelligence reports, the method comprising:

receiving, at a Software Development Kit ("SDK") component of a web intelligence report server, web intelligence data model authoring information, associated with a document, via an authoring Application Programming Interface ("API"), wherein the SDK component is to manage sessions, states, security, and resource access;

creating, by a compound database platform of an in-memory database, a report result via a data flow merge operation that combines multiple data sources into a single data source, based on the web intelligence data model authoring information, data sources associated with a plurality of data source types, and data access associated with a plurality of data layers;

storing the report result in a report repository;

receiving, by query facilities, web intelligence data model consumption information from a report engine and transmitting a get metadata message to the compound database platform; and executing, by a calculation engine, calculation plans on top of data stored in compound database platform, wherein the calculation receives web intelligence data model consumption information from the query facilities and transmits a get data message to the compound database platform, wherein the web intelligence data model is associated with a Web intelligence document as a data Source ("WaaS") reusable in other documents.

15. The medium of claim 14, wherein the compound database platform further performs data acquisition and creates a custom metadata layer.

16. The medium of claim 14, wherein the compound database platform contains at least one of: (i) a data provider definition, (ii) local storage for data flows provided by query execution, (iii) user objects with additional metadata definition, (iv) variables, (v) synchronized dimensions, (vi) grouping, (vii) geographic enrichments, and (viii) time enrichments.

17. The medium of claim 14, wherein each data source is associated with an abstract layer with a specific implementation to create queries and generate an executable statement.

18. The medium of claim 14, wherein the data access is associated with an abstract layer with a specific implementation for each data layer to execute a query statement and return result dataflows.

19. The medium of claim 14, wherein the SDK component is further to receive information engine and web intelligence SDK data.

* * * * *